Figure 2C:
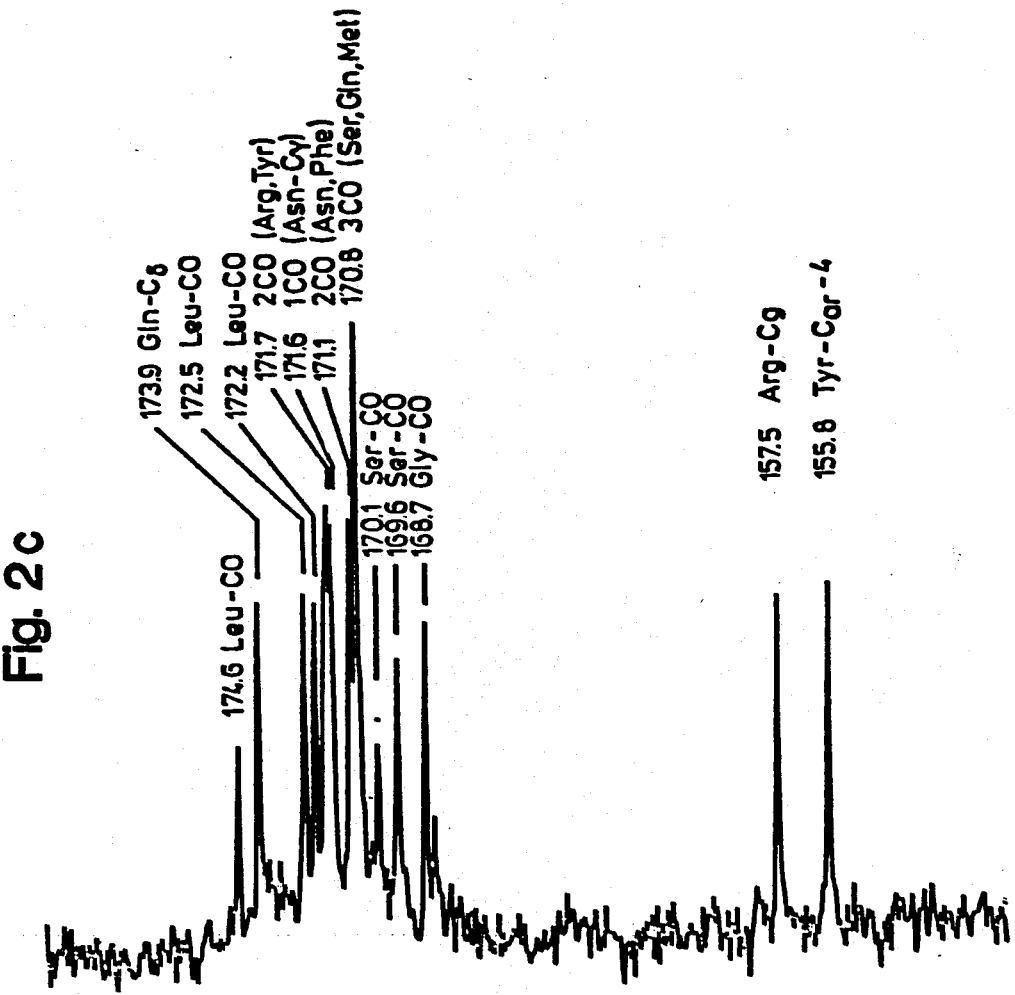

United States Patent [19]

Jung et al.

[11] 4,376,760

[45] Mar. 15, 1983

[54] TRIDECAPEPTIDE

[75] Inventors: Günther Jung, Tübingen; Hans Brückner, Ostfildern, both of Fed. Rep. of Germany; Peter Swetly, Vienna, Austria; Gerhard Bozler, Biberach an der Riss, Fed. Rep. of Germany

[73] Assignee: Dr. Karl Thomae Gesellschaft mit beschrankter Haftung, Biberach an der Riss, Fed. Rep. of Germany

[21] Appl. No.: 315,212

[22] Filed: Oct. 26, 1981

[30] Foreign Application Priority Data

Oct. 30, 1980 [DE] Fed. Rep. of Germany ....... 3040825

[51] Int. Cl.$^3$ ..................... G01N 33/00; A61K 39/00; C07C 103/52
[52] U.S. Cl. ...................................... 424/1.5; 424/85; 260/112.5 R
[58] Field of Search .................................. 424/1.5, 85; 260/112.5 R

[56] References Cited

PUBLICATIONS

E. Knight, Jr., et al., Science 207, 1980, 525, 526.
K. Zoon et al., Science 207, 1980, 527, 528.

Primary Examiner—Delbert R. Phillips
Attorney, Agent, or Firm—Hammond & Littell, Weissenberger & Muserlian

[57] ABSTRACT

The tridecapeptide of the formula

H-Met-Ser-Tyr-Asn-Leu-Leu-Gly-Phe-Leu-Gln-Arg-Ser-Ser-OH and the use thereof as a hapten, tracer or antibody.

3 Claims, 3 Drawing Figures

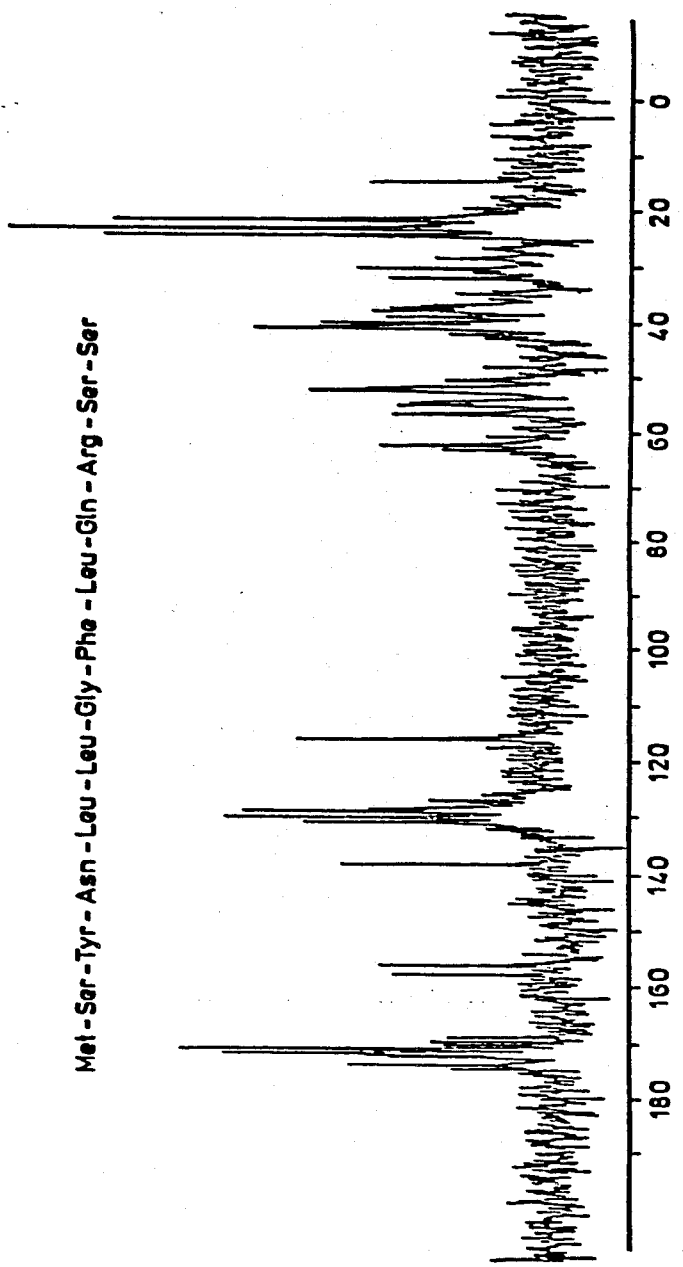

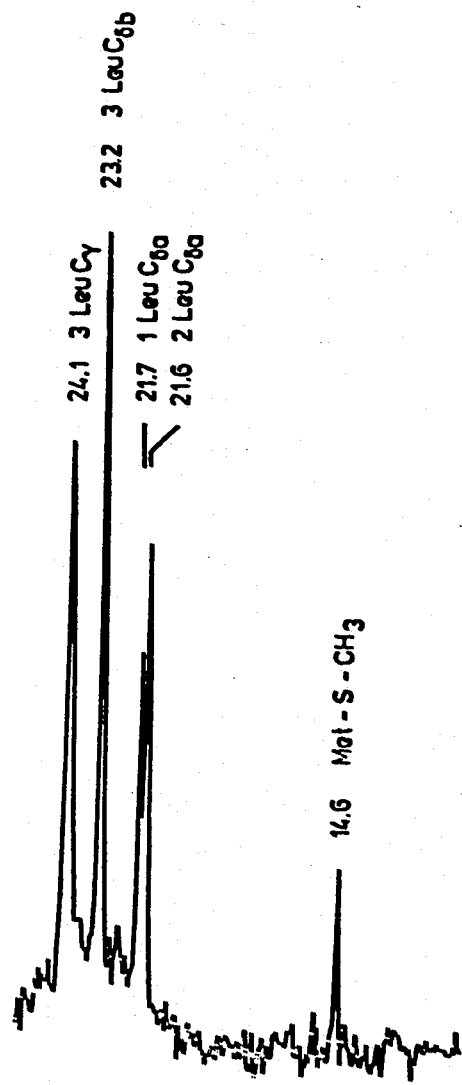

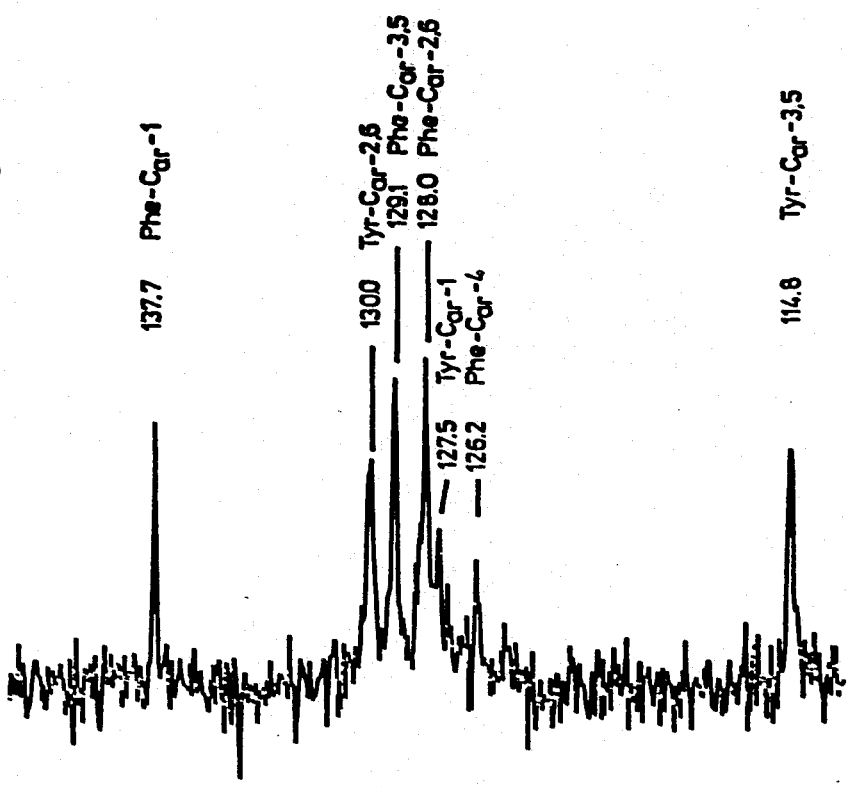

TRIDECAPEPTIDE

This invention relates to a novel tridecapeptide, to a process for its preparation by the solid-phase-synthesis, and to a method of using it as a hapten for coupling with an immunogen, for example.

The following conventional abbreviations used in peptide chemistry shall be used hereinafter:

| | |
|---|---|
| H—Ser—OH | = L-serine |
| H—Arg—OH | = L-arginine |
| H—Gln—OH | = L-glutamine |
| H—Leu—OH | = L-leucine |
| H—Phe—OH | = L-phenylalanine |
| G—Gly—OH | = glycine |
| H—Asn—OH | = L-asparagine |
| H—Tyr—OH | = L-tyrosine |
| H—Met—OH | = L-methionine |
| Bzl | = benzyl radical |
| 2,6-Cl$_2$—Bzl | = 2,6-dichlorobenzyl radical |
| Boc | = tert. butoxycarbonyl radical |
| Tos | = tosyl radical |
| DMF | = dimethylformamide |
| DCC | = N,N'—dicyclohexylcarbodiimide |
| HOBt | = 1-hydroxybenzotriazole |

Thus, the present invention relates to novel tridecapeptide H-Met-Ser-Tyr-Asn-Leu-Leu-Gly-Phe-Leu-Gln-Arg-Ser-Ser-OH.

BACKGROUND OF THE INVENTION

Highly purified interferon, which is a very interesting substance and is being investigated throughout the world, is today available for medical research only in very small amounts. Therefore, it has heretofore not been possible to subject interferon-proteins to structural or biochemical investigations. Since the N-terminal sequence of human lymphoblast-interferon has now been elucidated [Science 207, 525–526 (1980)], the tridecapeptide of the instant invention has for the first time been synthesized and its properties investigated.

DESCRIPTION OF THE INVENTION

The tridecapeptide of the present invention is prepared by the solid-phase-synthesis [see Merrifield, J.A.C.S. 85, 2149–2154 (1963)]. In this method the C-terminal aminoacid of a peptide is attached by way of its carboxyl group to a polymer which serves as an insoluble carrier. If a chloromethyl-resin is used as the polymer, the attachment is effected either preferably by means of an alkali metal or alkaline earth metal salt of the corresponding N-protected aminoacid, or if a hydroxymethyl-resin is used as the polymer by activation of the carboxyl function of the corresponding N-protected aminoacid, for example with dicyclohexyl-carbodiimide. This step is followed by the stepwise build-up of the peptide by stepwise attachment of the individual aminoacids to the N-end of the peptide fragment, and subsequent removal of the amino-protective group. The attachment of the next following N-protected aminoacid to the now free and reactive terminal amino group of the peptide fragment is effected by activation of its carboxyl function or by means of a reactive ester. After completion of the build-up of the aminoacid sequence the peptide is removed from the insoluble carrier resin.

The presence of the amino acids serine, tyrosine and arginine makes it necessary to provide additional protection for the side functions, for example by converting them into the corresponding O-benzylserine, O-2,6-dichlorobenzyl tyrosine and N$^g$-tosyl-arginine derivatives.

A swellable polymer, such as chloromethylated polystyrene which is preferably cross-linked with a 1% divinylbenzene (PS-1% DVB), is preferably used in the solid-phase-synthesis of the present invention.

In a particularly advantageous embodiment of the process according to the present invention, serine in its protected form, such as

Boc-Ser(Bzl)-OH is esterified by means of its cesium salt as the first aminoacid onto chloromethylated polystyrene in a solvent, preferably in an aprotic solvent such as dimethyl-formamide. The cesium salt is advantageously obtained by reacting the above-mentioned protected aminoacid with cesium carbonate or cesium hydroxide. Thereafter, the amino-protective group which is used is split off; for instance, a tert. butoxy-carbonyl group is removed with an acid such as 50% trifluoroacetic acid in dichloromethane, preferably after first washing with dichloromethane.

In each subsequent synthesis cycle the resulting product is coupled with an excess of the corresponding Boc-aminoacid or its activated ester, for example with 3- to 6-fold the required amount, optionally in the presence of a coupling reagent such as N,N'-dicyclohexylcarbodiimide, and this procedure is repeated several times, such as 2 to 5 times, without prior testing for possibly still present free amino groups, with a further comparable excess of the corresponding Boc-aminoacid and coupling reagent or its activated ester (post-coupling). After first washing, the Boc protective group is split off as described above.

This synthesis cycle is repeated with the particular N-protected aminoacids or their reactive esters until the desired protected tridecapeptide resin is obtained.

The aminoacid derivatives Boc-Gln and Boc-Asn are preferably coupled by means of a reactive ester thereof, such as their p-nitro-phenyl esters. Furthermore, 1-hydroxy-benzotriazole may be added as a catalyst in the coupling or post-coupling procedures.

After each synthesis cycle the product is acetylated with acetic acid anhydride/N-methyl-morpholine to block, prior to the next coupling, any amino group of the peptide fragment which may have been left unreacted in the previous coupling procedure. Moreover, after about the ninth synthesis cycle, more intensive swelling of the peptide resin was observed, which means that, particularly in the treatment with trifluoroacetic acid/dichloromethane, substantially more reagent solution is required than in the first synthesis cycles.

After the synthesis is complete, the Boc and Bzl groups are removed by adding hydrogen bromide to the suspension of the peptide resin in trifluoroacetic acid, with the addition of resorcinol and thioanisole, and the N$^g$-tosyl-tridecapeptide formed is split off from the solid phase which is used. The N$^g$-tosyl-tridecapeptide thus obtained and purified by reprecipitation is treated with sodium in liquid ammonia in order to splitt off the tosyl group. For further purification, the tridecapeptide thus obtained is reprecipitated, for instance from glacial acetic acid/ether and dimethylformamide/acetone, chromatographed on a column of gel, such as Sephadex G 25, with glacial acetic acid/water (1/1), and finally subjected to multiplicative counterflow distribution, for example with 1-butanol/5% acetic acid/1-propanol (10/10/2) as the two-phase system.

Thus, the solid-phase-synthesis for the preparation of the partially protected tridecapeptide and the tridecapeptide free from protective groups is effected in accordance with the present invention pursuant to the following reaction scheme:

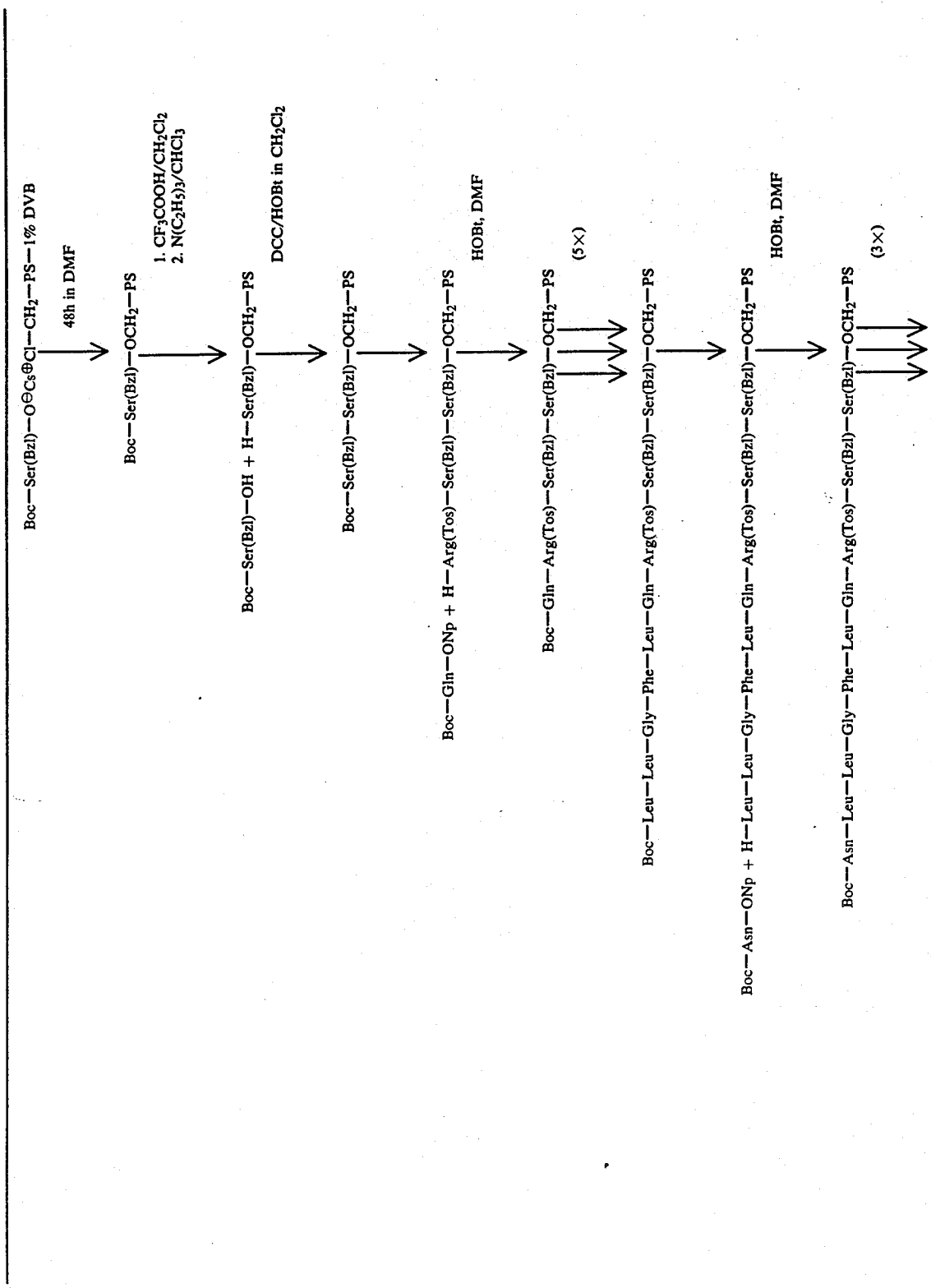

-continued

Figure 3:
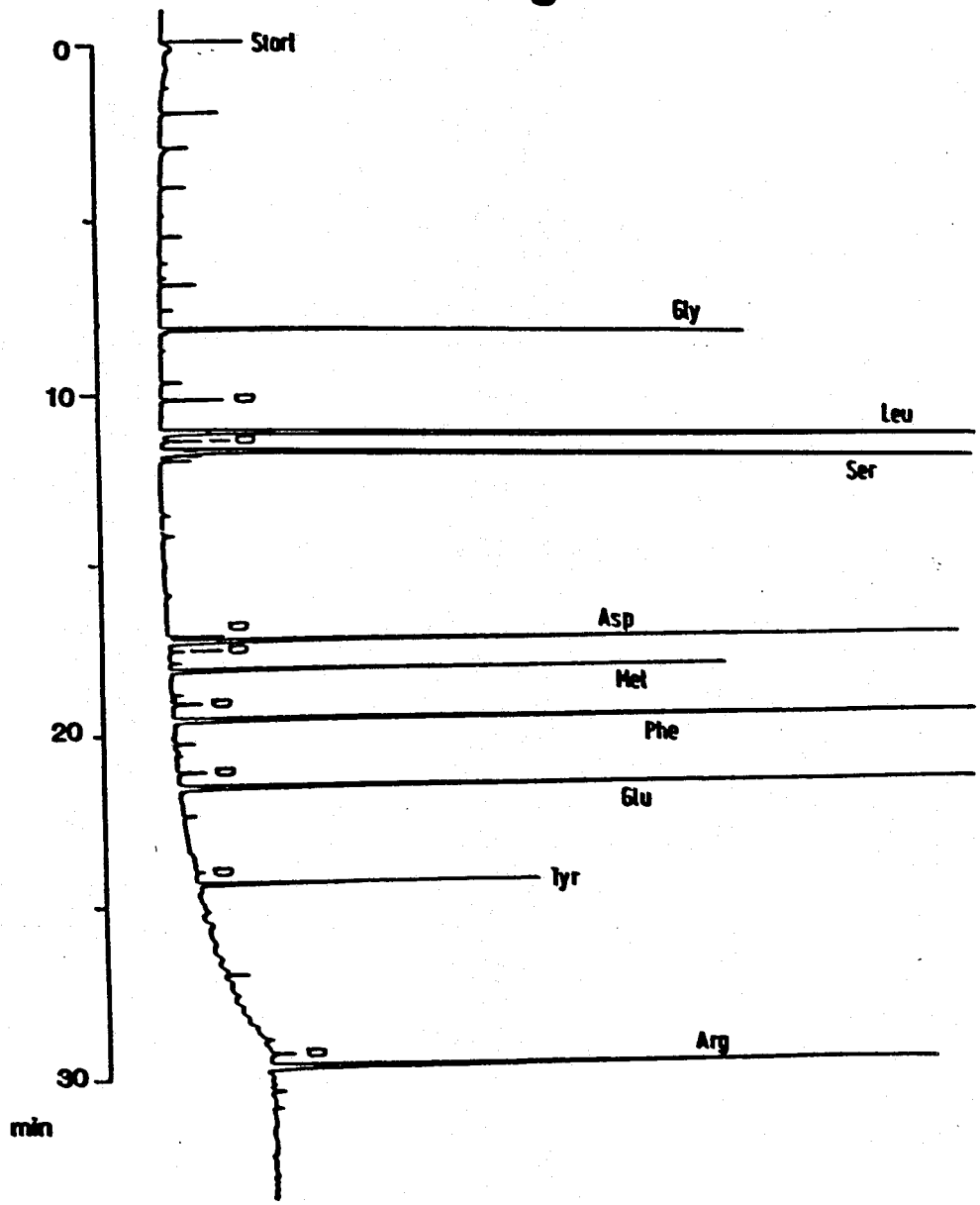

Boc—Met—Ser(Bzl)—Tyr(2,6-Cl₂—Bzl)—Asn—Leu—Leu—Gly—Phe—Leu—Gln—Arg(Tos)—Ser(Bzl)—Ser(Bzl)—OCH₂—PS $\xrightarrow{\text{HBr/CF}_3\text{COOH, 90 min}}$ H—Met—Ser—Tyr—Asn—Leu—Leu—Gly—Phe—Ley—Gln—Arg(Tos)—Ser—Ser—OH $\xrightarrow{\text{Na, NH}_3 \text{ fl.}}$ H—Met—Ser—Tyr—Asn—Leu—Leu—Gly—Phe—Leu—Gln—Arg—Ser—Ser—OH In the accompanying drawings FIGS. 1, 2a, 2b and 2c are the $^{13}$C-NMR-spectra of the tridecapeptide Met-Ser-Tyr-Asn-Leu-Leu-Gly-Phe-Leu-Gln-Arg-Ser-Ser; and FIG. 3 is the gas-chromatogram of the n-propyl esters of the N-pentafluoropropionyl-aminoacid of a hydrolyzate of the free tridecapeptide on chiral phase.

The following examples illustrate the present invention and will enable others skilled in the art to understand it more completely. It should be understood, however, that the invention is not limited solely to the particular examples given below. Obviously, the decapeptide may also be synthesized in a similar manner using other condensation processes commonly used in peptide chemistry and other conventional protective groups.

EXAMPLE OF SOLID-PHASE-SYNTHESIS

I. Preparation of the protected tridecapeptide on the carrier

Stage 1

6.0 gm (20 mmols) of Boc-Ser(Bzl)-OH were neutralized to pH 6–7 in 70 ml of ethanol/water (7:2), using a pH meter, with an aqueous solution of about 3.2 gm (10 mmols) of cesium carbonate. After evaporation in vacuo, the remaining water was removed azeotropically with benzene. After drying at 0.1 mbar over diphosphorus pentoxide/potassium hydroxide, the cesium salt which had solidified in vitreous form was dissolved in 50 ml of dimethylformamide and slowly stirred with 15 gm of Merrifield resin (polystyrene-1% divinylbenzene, 0.9 mequ. Cl/gm) at 50° C. for 48 hours. The resin was then washed with three batches of 50–100 ml of dimethylformamide, dimethylformamide/water (9:1), 95% ethanol, anhydrous ethanol, dioxane, ethanol, chloroform, ethanol, dichloromethane, methanol and dried in vacuo over phosphorus pentoxide. The charge, determined by amino acid analysis, was 0.25 mmol/gm.

Stage 2

The Merrifield resin esterified with Boc-Ser(Bzl)-OH was washed with 2×100 ml of dichloromethane. To split off the Boc protective group, 100 ml of dichloromethane/trifluoroacetic acid mixture (v/v, 1:1) were added; after 5 minutes, suction filtering was carried out, and the product was mixed with fresh reaction solution of the same composition. After 20 minutes, it was washed three times, each time with 100 ml of dichloromethane and then dichloromethane/dioxan (v/v, 2:1). The amino function of the serine group was then deprotonated with 100 ml of triethylamine/chloroform (v/v, 1:9). After two minutes, the amine solution was replaced by fresh solution. After 5 minutes, the mixture was washed once with 100 ml of chloroform and three times with 100 ml of dichloromethane. For coupling, the resin was suspended for 10 minutes with 6 gm (20 mmols) of Boc-Ser(Bzl)-OH in 50 ml of dichloromethane, and then 20 mmols (4.12 gm) of DCC in 20 ml of dichloromethane were added. For post-coupling, another 10 mmols of Boc-Ser(Bzl)-OH and 10 mmols of DCC, both dissolved in a little dichloromethane, were added after 30 minutes. After a total coupling period of 2 hours, the product was washed three times, each time with 100 ml of dichloromethane and DMF. 5 ml of acetic anhydride in 40 ml DMF, followed by 3 gm of N-methyl morpholine in 40 ml of DMF, were then added. After 20 minutes, the product was washed three times, each time with 100 ml of DMF, ethanol and dichloromethane.

Stage 3

Coupling with 8.6 gm (20 mmols) of Boc-Arg(Tos)-OH, post-coupling with 4.3 gm (10 mmols) of Boc-Arg(Tos)-OH analogous to Stage 2. The Boc-Arg(Tos)-OH, which is not readily soluble in dichloromethane, was first dissolved in some DMF, and only then was it added to dichloromethane.

Stage 4

After splitting off the Boc-protective group analogous to Stage 2, 7.35 gm (20 mmols) of Boc-Gln-ONp were dissolved in 70 ml of DMF and added to the tripeptide resin. After half an hour's reaction, 20 mmols of HOBt were added and, for post-coupling, after another 60 minutes, 14.7 gm (40 mmols) of Boc-Gln-OH, 40 mmols of HOBt and 20 mmols of N,N'-dicyclohexyl-carbodiimide were added. After 30 minutes' reaction, the resin was washed three times with DMF, then allowed to react for 10 minutes with a mixture of 3 ml of acetic acid anhydride in 40 ml of DMF and 1.5 gm of N-methyl-morpholine in 40 ml of DMF and 1.5 gm of N-methylmorpholine in 40 ml of DMF, then washed three times with DMF, three times with absolute ethanol and three times with dichloromethane.

Stage 5

After splitting off the Boc-protective group and neutralizing analogous to Stage 2, 7.5 gm (30 mmols) of Boc-Leu-OH×H$_2$O (pre-dried) were dissolved in 20 ml of dimethylformamide, added to the tetrapeptide resin, and 30 ml (30 mmols) of a 1 M N,N'-dicyclohexyl-carbodiimide solution in dichloromethane were added. After one and a half hours' reaction, for post-coupling, 7.5 gm (30 mmols) of Boc-Leu-OH×H$_2$O, 30 mmols of a 1 M N,N'-dicyclohexyl-carbodiimide solution in dichloromethane and 4.05 gm (30 mmols) of HOBt were added. After 2¼ hours' reaction, the product was washed once with dichloromethane, twice with dioxane and three times with dimethylformamide. Then it was treated with 6 ml of acetic acid anhydride in 40 ml of dimethylformamide and with 3 gm of N-methyl-morpholine in 40 ml of dimethylformamide (reaction time: 10 minutes). It was then washed three times with dimethylformamide, three times with ethanol and three times with dichloromethane.

Stage 6

Coupling with 5.3 gm (20 mmols) of BOC-Phe-OH, post-coupling with 5.3 gm (20 mmols) of BOC-Phe-OH analogous to Stage 2.

Stage 7

Coupling with 3.5 gm (20 mmols) of BOC-Gly-OH, post-coupling with 3.5 gm (20 mmols) of BOC-Gly-OH analogous to Stage 2.

Stage 8

Coupling with 5.0 gm (20 mmols) of BOC-Leu-OH×H$_2$O, post-coupling with 4.25 gm (17 mmols) of BOC-Leu-OH×H$_2$O analogous to Stage 5.

Stage 9

Coupling with 5.0 gm (20 mmols) of BOC-Leu-OH×H$_2$O, post-coupling with 4.25 gm (17 mmols) of BOC-Leu-OH×H$_2$O, analogous to Stage 5.

Stage 10

Coupling with 7.0 gm (20 mmols) of BOC-Asn-ONp, post-coupling with 7.0 gm (20 mmols) of BOC-Asn-ONp analogous to Stage 4.

Stage 11

Coupling with 8.8 gm (20 mmols) of BOC-Tyr(O-2,6-Cl$_2$-Bzl)-OH, post-coupling with 8.8 gm (20 mmols) of BOC-Tyr(O-2,6-Cl$_2$-Bzl)-OH analogous to Stage 2.

Stage 12

Coupling with 6.0 gm (20 mmols) of BOC-Ser(Bzl)-OH, post-coupling with 6.0 gm (20 mmols) of BOC-Ser(Bzl)-OH analogous to Stage 2.

Stage 13

Coupling with 5.0 gm (20 mmols) of BOC-Met-OH, post-coupling with 5.0 gm (20 mmols) of BOC-Met-OH analogous to Stage 2.

II. Removal of the peptide from the carrier

After the last washing with dichloromethane, the peptide resin was dried over diphosphorus pentoxide/potassium hydroxide for 15 hours in vacuo. The Arg$^{11}$-(Tos)-tridecapeptide was then split off with HBr in trifluoroacetic acid solution (250 ml) at room temperature. The wash bottles for the HBr gas and the reaction vessel contained 3% of resorcinol and thioanisole. After 120 minutes, the resin was separated by suction-filtering, and the trifluoroacetic acid solution was immediately evaporated in a rotary evaporator (20° C. bath temperature). The oily residue was dissolved in 150 ml of glacial acetic acid/water (3:1) and again evaporated at 40° C. bath temperature. The residue was dissolved in about 800 ml of tert. butanol/water (1:1) and lyophilized. A colorless lyophilizate was obtained. The lyophilizate was not readily soluble in water or the majority of organic solvents. It was reprecipitated from glacial acetic acid/water and glacial acetic acid/ether, and in a number of solvents it solidified in the form of a gel. It was reprecipitated once more from dimethylformamide/methanol/chloroform (7:4:3) solution by the addition of ether. The jelly-like precipitate could be suction-filtered on a frit and was dried in vacuo over diphosphorus pentoxide/potassium hydroxide. Yield: 15.65 gm of Arg$^{11}$(Tos)-tridecapeptide.

III. Removal of the tosyl protective group 5 gm of dry Arg$^{11}$(Tos)-tridecapeptide were added to 500 ml of liquid ammonia and mixed with an Na/NH$_3$ solution until there was a stable blue coloration. 15 seconds later, NH$_4$Cl is added. The ammonia was then blown off with dry N$_2$, and the residue was dissolved in glacial acetic acid/water (1:1). After evaporation in a rotary evaporator to about 30 ml, the peptide solution was stirred into 120 ml of water in centrifuge beakers. The tridecapeptide precipitated as a thick, colorless solid which was washed three times with water by centrifuging.

IV. Chromatographic purification of the tridecapeptide

The crude tridecapeptide was coarse-chromatographed on Sephadex G 25. Column: 5×90 cm; eluant:- glacial acetic acid/water (1:1); flow rate: 7.15 ml/10 min. While still moist, the tridecapeptide was dissolved by the addition of the same volume of glacial acetic acid. The solution, amounting to about 75 ml, was added all at once. The 18 ml-fractions were analyzed by thin-layer chromatography on silicagel plates in a system consisting of 1-butanol/glacial acetic acid/water (3:1:1) (spray reagent: chlorine/4,4'-bis(dimethylamino)diphenyl-methane). The peptide appeared in the elution volume 422–792 ml. The combined fractions were evaporated in vacuo, and the residue was dissolved in about 20 ml of glacial acetic acid. This solution was slowly added dropwise to anhydrous ether, while stirring. The peptide thereby precipitated as completely colorless, rapidly settling flakes. It was washed three times with anhydrous ether in a centrifuge. After drying in vacuo, 3.1 gm of powdered product remained, which were further purified by precipitation from dimethylformamide with acetone. Examination by thin-layer chromatography, using the system described above, showed that the peptide was substantially pure. The amino acid analysis gave the expected values and showed a peptide content of 43%.

V. Purification of the tridecapeptide by multiplicative counterflow distribution 0.5 gm of tridecapeptide was dissolved in a distribution system of 1-butanol/5% acetic acid/1-propanol (5:5:1) while stirring. The solution wad distributed between the first 15 tubes of a Craig apparatus (10 ml elements) over 120 stages. Any lipophilic impurities, presumably N-acetyl-peptides, judging from the amino acid analysis, run to the front, and any impurities containing salts are left at the start in the aqueous phase. According to thin-layer chromatography (system: 1-butanol/glacial acetic acid/water (3:1:1), R$_f$0.25), completely pure tridecapeptide was obtained with r$_{max}$=45. Yield: 150 mg.

The identity of the tridecapeptide obtained in the preceding example was confirmed by amino acid analysis, $^{13}$C-NMR spectroscopy and by racemate determination.

The amino acid analysis was carried out in a Biotronik amino acid analyzer LC 600 E. The hydrolysis was effected with 6 N hydrochloric acid at 110° C. over a period of 18 to 72 hours. H-Ser-OH, H-Met-OH and H-Tyr-OH were partially destroyed during the hydrolysis, but the Leu-Leu bond was not completely broken until 72 hours had elapsed. Without correction of the hydrolysis losses, the following composition of amino acids was found:

TABLE 1

| Amino acid | Number of amino acid groups | |
|---|---|---|
| | Found | Calculated |
| Asp | 1.00 | 1 |
| Ser | 2.71 | 3 |
| Glu | 1.06 | 1 |
| Gly | 1.07 | 1 |
| Met | 0.89 | 1 |
| Leu | 2.60 | 3 |
| Tyr | 0.77 | 1 |
| Phe | 1.00 | 1 |
| Arg | 1.00 | 1 |

Investigation by gas chromatography, using the n-propyl ester of N-pentafluoropropionylamino acid of the total hydrolyzate of the tridecapeptide at the chiral phase Chirasil-Val [J. Chromatogr. 146, 197 (1978)] showed a very high enantiomeric purity of the amino acid group of the tridecapeptide (see FIG. 3).

The $^{13}$C-NMR spectra were measured at 30° C. in a WH-90 NMR-spectrometer made by Bruker-Physik of Karlsruhe, Germany. Because of the poor solubility of the tridecapeptide, a $^{12}C,^{2}H$-dimethylsulfoxide solution was used. At a concentration of 60 mg/ml and with an accumulation period of 12 hours, a $^{13}C$-NMR spectrum (20.115 MHz) with relatively good resolution was obtained, which clearly showed the identity of the new tridecapeptide with the sequence 1 to 13 (FIG. 1). It shows particularly clearly the singularly occurring characteristic signals of the S-methyl group of methionine (14.6 ppm), the 6 methyl groups (21.6–23.2 ppm) and the C-carbons (24.1 ppm) of the three leucine groups in the top part of the spectrum (FIG. 2a). In the aromatic range, there are no problems in identifying the aromatic signals of phenylaniline and tyrosine (FIG. 2b). Moreover, the resonance signals at 155.8 ppm (phenolic C-4 carbon of the tyrosine) and at 157.5 ppm (guanidino carbon of the arginine) indicate the structure. It should be noted that the intensities of these typical signals are comparable, even though these amino acids are positionally far apart in the sequence. The carbonyl part of the spectrum also, as expected, contained 15 signals of comparable intensities (FIG. 2c). This indicates the presence of a very uniform peptide.

The tridecapeptide was also characterized by its CD spectrum in trifluoroethanol and trifluoroethanol/hexafluoroacetone-sesquihydrate solutions. The peptide had a helical configuration which produced negative Cotton-effects with maxima at 223 and 207 nm.

The tridecapeptide of the present invention is useful as a hapten which is coupled, according to known methods, to a natural protein, such as human serum albumin, cattle serum albumin, egg albumin, or to a synthetic polypeptide such as poly-L-lysine, poly-L-alanyl-L-lysine or to other carriers such as modified dextrans. The peptide can also be linked via other polyamines such as 1,6-diaminohexane. An immunogen thus produced, or the tridecapeptide itself, can be used in conjunction with known methods for the production of antisera or antibodies against human fibroblast interferon.

The novel tridecapeptide may be used in a suitable preparation for therapy, instead of human fibroblast interferon.

The novel tridecapeptide is useful as a tracer for the immunological determination of human fibroblast interferon. For this purpose, it may, on the one hand, be labeled directly according to known methods, for instance with radioactive iodine or other suitable markers, for example with enzymes such as peroxidases, or with fluorescent compounds. On the other hand, it may also be labeled by the same or similar methods, in the form of the above-mentioned coupling products, and be used as a tracer.

The new tridecapeptide can also be used in the form of a coupling product with an immobile carrier, such as dextrans, sepharose or polystyrene, or modified inorganic carriers such as Biogel or CPG-10, for isolating and purifying antibodies against human fibroblast interferons. Antibodies thus obtained can be used, in known manner, for the purification and isolation of human fibroblast interferon.

The fully protected tridecapeptide found on the carrier after the stepwise synthesis can also be split off from the carrier in protected form, for instance by hydrazinolysis, hydrolysis or exchange of ester radicals. These partically or fully protected tridecapeptide derivatives which are split off also constitute useful intermediate products for the synthesis of higher peptides of fibroblast interferon or for the synthesis of fibroblast interferon itself.

The following examples describe various possible applications of the novel tridecapeptide:

EXAMPLE A

Coupling of the tridecapeptide to poly-L-lysine for the production of an immunogen which is useful for obtaining antisera against human fibroblast interferon 46.9 mg of poly-L-lysine hydrobromide (molecular mass 37,300; 0.223 mmol amino functions) were dissolved in 0.3 ml of water, about pH 4, and adjusted to about pH 9.5 with 5 μl of triethylamine, while stirring. Then, 2 N hydrochloric acid was added to give a pH of 7.5, and then 57.3 mg (0.038 mmol) of tridecapeptide (molecular mass 1516), dissolved in 2.5 ml of dimethylformamide, were added while heating, and 389.3 mg (1.890 mmols) of N,N'-dicyclohexylcarbodiimide, dissolved in 0.5 ml of dimethylformamide, were added. After 24 hours at room temperature, the conjugate was precipitated with ether and washed with ether. It was then dissolved in water with the addition of a little formic acid and dialyzed against water for 48 hours (exclusion limit 8000) and then lyophilized.

Yield: 52 mg; charge: 17.8 mols tridecapeptide per 1 mol poly-L-lysine.

EXAMPLE B

Iodine labeling of the coupling product of the tridecapeptide to poly-L-lysine

Of the dry coupling product to poly-L-lysine, 2 mg were weighed out and dissolved in 52 μl of a mixture of 25 μl of water, 25 μl of dimethylsulfoxide and 2 μl of glacial acetic acid. This solution was diluted with a sodium borate buffer. 12 μl thereof, with a borate concentration of 0.1 M, pH 9.0, and of 10 μg/μl coupling product, were transferred at a temperature of 0° C. (on ice) into a reaction vessel in which BOLTON-HUNTER reagent (N-hydroxysuccinimide ester of p-hydroxy-phenylpropionic acid iodized with $^{125}I$) had been dried with benzene.

The reaction was stopped after one hour by the addition of 90 μl of 0.3 M glycine in 0.1 M sodium borate, pH 9.0. After another 10 minutes, the entire volume was poured onto a chromatography column (7 ml bed volume, Sephadex G 25 Medium (Pharmacia, Uppsala), which had been equilibrated with 50 mM sodium phosphate, pH 7.5, and 0.25% gelatine, and which was also developed in this buffer. The high-molecular labeled substance was separated from the low-molecular radioactive reaction products and appeared in the first fractions of the void volume.

A better yield, compared to these original instructions laid down by BOLTON and HUNTER, was obtained when the solution was adjusted to an acidic pH after the reaction had ended. After the addition of glycine, the pH was adjusted from 9 to 4 by further addition of 100 μl of 20 mM sodium acetate, pH 4.0. The chromatography column was accordingly pretreated with 20 mM sodium acetate, pH 4.0, and 0.25% gelatine, and was developed in this buffer.

Starting from a radioactivity of 0.2 mCi of BOLTON-HUNTER reagent with a specific radioactivity of 2000 Ci/mmol, a labeling of at least $10^4$ cpm (counts per minute)/μg of coupling product was obtained.

EXAMPLE C

Preparation of coupling products of the tridecapeptide with AH-Sepharose 4 B for the isolation and purification of antibodies against human fibroblast interferon The free carboxyl group of the tridecapeptide was coupled to the amino groups of AH-Sepharose 4B (Pharmacia) by means of carbodiimide. For this purpose, 500 mg of AH-Sepharose 4B were suspended in 5 ml of dimethylformamide/water, pH 4.5, and mixed with 30.3 mg (0.02 mmol) of tridecapeptide dissolved in DMF. After the dropwise addition of 300 mg of N-ethyl-N'-(3-dimethylaminopropyl)-carbodiimide hydrochloride (EDC) in a little water, the reaction mixture was shaken for 12 hours at room temperature. Then, the gel was washed with DMF/water (4:1), dioxane/water (1:1) and with water until the filtrate was free from excess EDC, tridecapeptide and N-ethyl-N'-dimethylaminopropyl-urea.

EXAMPLE D

Preparation of coupling products of the tridecapeptide with lysine-Sepharose 4B for affinity chromatography Coupling of 30.3 mg (0.02 mmol) of tridecapeptide with 500 mg of lysine-Sepharose 4B (Pharmacia) analogous to Example C.

EXAMPLE E

Preparation of coupling products of the tridecapeptide with aminopropyl-CPG-10 for affinity chromatography 30 mg of tridecapeptide were coupled, with the aid of carbodiimide, to 500 mg of Controlled-Pore Glass CPG-10, charged with aminopropyl groups, pore size 75, and 120 Ångströms in diameter. Reaction conditions analogous to Example C.

EXAMPLE F

Coupling of the tridecapeptide to 1,6-diamino-hexane 20.6 mg (100 μmols) of N,N'-dicyclohexyl-carbodiimide were added to 15.16 mg (10 μmols) of tridecapeptide and 0.58 mg (5 μmols) of 1,6-diamino-hexane in 2 ml of DMF. The progress of the reaction was monitored by thin-layer chromatography, using the system 1-butanol/glacial acetic acid/water (3:1:1). After coupling had ended, the reaction solution was added dropwise to 5 ml of ether, while stirring. The precipitate formed was washed twice with ether by centrifuging. The product was then chromatographed on Sephadex LH 20 to separate the monoadduct (eluant: DMF, column 1×50 cm, detection by TLC). Alternatively, the product can be purified by preparative thin-layer chromatography.

While the present invention has been illustrated with the aid of certain specific embodiments thereof, it will be readily apparent to other skilled in the art that the invention is not limited to these particular embodiments, and that various changes and modifications may be made without departing from the spirit of the invention or the scope of the appended claims.

We claim:

1. The tridecapeptide of the formula H-Met-Ser-Tyr-Asn-Leu-Leu-Gly-Phe-Leu-Gln-Arg-Ser-Ser-OH.

2. The $Arg^{11}$-(Tos)-tridecapeptide of the formula H-Met-Ser-Tyr-Asn-Leu-Leu-Gly-Phe-Leu-Gln-Arg(Tos)-Ser-Ser-OH.

3. The method of using the tridecapeptide of claim 1 as a hapten, tracer or antibody.

* * * * *